United States Patent
Cohen et al.

(10) Patent No.: US 7,512,633 B2
(45) Date of Patent: Mar. 31, 2009

(54) CONVERSION OF HIERARCHICALLY-STRUCTURED HL7 SPECIFICATIONS TO RELATIONAL DATABASES

(75) Inventors: Simona Cohen, Haifa (IL); Yossi Mesika, Afula (IL)

(73) Assignee: International Business Machines Corporation, Armonk, NY (US)

( * ) Notice: Subject to any disclaimer, the term of this patent is extended or adjusted under 35 U.S.C. 154(b) by 411 days.

(21) Appl. No.: 11/180,098

(22) Filed: Jul. 13, 2005

(65) Prior Publication Data

US 2007/0016610 A1    Jan. 18, 2007

(51) Int. Cl.
    *G06F 17/00*    (2006.01)
(52) U.S. Cl. ............... 707/104.1; 707/101; 707/102; 707/103 X; 717/108; 717/116
(58) Field of Classification Search ............ 707/1, 707/2, 3, 4, 5, 6, 7, 8, 9, 101, 102, 103, 104
    See application file for complete search history.

(56) References Cited

U.S. PATENT DOCUMENTS

| | | | | |
|---|---|---|---|---|
| 5,809,499 | A * | 9/1998 | Wong et al. ............... | 707/6 |
| 6,163,781 | A | 12/2000 | Wess, Jr. ............... | 707/103 X |
| 6,519,601 | B1 * | 2/2003 | Bosch ............... | 707/100 |
| 6,529,909 | B1 | 3/2003 | Bowman-Amuah ...... | 717/126 |
| 6,550,057 | B1 * | 4/2003 | Bowman-Amuah ...... | 717/126 |
| 6,741,981 | B2 * | 5/2004 | McGreevy ............... | 707/3 |
| 6,920,502 | B2 * | 7/2005 | Araujo et al. ............ | 709/229 |
| 6,954,757 | B2 * | 10/2005 | Zargham et al. ......... | 707/101 |
| 7,072,896 | B2 * | 7/2006 | Lee et al. ............... | 707/101 |
| 7,167,873 | B2 * | 1/2007 | Brobst et al. ........... | 707/104.1 |
| 7,219,090 | B2 * | 5/2007 | Travis, Jr. ............... | 707/3 |
| 7,346,889 | B1 * | 3/2008 | Semenov et al. ......... | 717/106 |
| 2002/0107864 | A1 * | 8/2002 | Battas et al. ............ | 707/101 |
| 2003/0023580 | A1 * | 1/2003 | Braud et al. ............ | 707/3 |
| 2003/0088438 | A1 * | 5/2003 | Maughan et al. ........ | 705/2 |
| 2003/0088543 | A1 * | 5/2003 | Skeen et al. ............ | 707/1 |
| 2004/0064447 | A1 * | 4/2004 | Simske et al. ........... | 707/5 |
| 2004/0141661 | A1 * | 7/2004 | Hanna et al. ............ | 382/305 |
| 2005/0187794 | A1 * | 8/2005 | Kimak ............... | 705/3 |
| 2005/0240621 | A1 * | 10/2005 | Robertson et al. ...... | 707/102 |
| 2006/0155581 | A1 * | 7/2006 | Eisenberger et al. .... | 705/3 |
| 2006/0206523 | A1 * | 9/2006 | Gaurav et al. ........... | 707/104.1 |

OTHER PUBLICATIONS

Jason Lyman, Applying the HL7 Reference Information Model To a Clinical Data Warehouse, IEEE, 5 vol (Iixv+Iii+5045), 4249-4255.*

(Continued)

*Primary Examiner*—Pierre M Vital
*Assistant Examiner*—Mohammad S Rostami

(57) ABSTRACT

A method for storing communication messages in a relational database includes accepting an object model including data elements and associations between the data elements, derived from a hierarchically-structured HL7 specification. A relational database that represents the object model is defined based on the data elements and the associations and may be augmented with configured domain knowledge. A communication message conforming to the HL7 specification is received. The message includes data items corresponding to one or more of the data elements. The data items are stored in the relational database so as to preserve the associations between the data items, as defined in the object model.

13 Claims, 5 Drawing Sheets

OTHER PUBLICATIONS

Robert H. Dolin, Nov./Dec. 2001, The HL7 Clinical Document Architecture, Journal of the American Medical Informatics Association, vol. 8, No. 6, pp. 552-569.*

DB2® produced by IBM Corporation (Armonk, New York), details at www-306.ibm.com/software/data/db2/.

Oracle® produced by Oracle Corporation (Redwood Shores, California), details at www.oracle.com.

Microsoft® Office Access produced by Microsoft Corporation (Redmond, Washington), details at www.office.microsoft.com.

Ambler, "Mapping Objects to Relational Databases," Jul. 2000 available at www-106.ibm.com/developerworks/webservices/library/ws-mapping-to-rdb/.

Zhang and Dewey, "Elecronic Medical Record Systems and Databases," May 2001, available at : icmit.mit.edu/sxzhang/healthcare/word.htm.

Shanmugasundaram et al., "Relational Databases for Querying XML Documents: Limitations and Opportunities", Proceedings of the 25th Very Large Data Bases Conference (VLDB'99), Edinburgh, Scotland, Sep. 1999, pp. 302-314. http://citeseer.ist.psu.edu/cache/papers/cs/14116/http:zSzzSzwww-personal.umich.eduzSz~krunaponzSzresearchzSzxmlzSzRdbmsForXML.pdf/relational-databases-for-querying.pdf.

SkyHawk Systems (San Jose, California) database middleware package called "Connect XML-2-DB", www.skyhawksystems.com/.

Robert Bourret (Felton, California), "XML-DBMS," available at www.rpbourret.com/xmldbms/.

Dolin, et al., "HL7 Clinical Document Architecture, Release 2, Committee Ballot #02," Dec. 8, 2003, published by the HL7 Structured Documents Technical Committee. The CDA specification documentation is also available at http://www.hl7.org/v3ballot/html/infrastructure/cda/cda.htm.

Unified Modeling Language (UML) (Details regarding UML can be found at http://www.uml.org/.).

Chamberlin, "A Complete Guide to DB2 Universal Database," Morgan Kaufman Aug. 1998, pp. 80-103: 2.6 Data Definition.

D B2 XML Extender produced by IBM. Details at www-306.ibm.com/software/data/db2/extenders/xmlext/.

* cited by examiner

CONVERSION OF HIERARCHICALLY-STRUCTURED HL7 SPECIFICATIONS TO RELATIONAL DATABASES

FIELD OF THE INVENTION

The present invention relates generally to healthcare computer systems, and particularly to methods and systems for storing healthcare-related information in relational databases.

BACKGROUND OF THE INVENTION

Health Level Seven (HL7) is a standards-producing body, which develops data standards for storing and exchanging information across the healthcare industry. The HL7 standards cover both clinical and administrative aspects of the healthcare industry, including laboratory, clinical genomics, medical records, patient care, pharmacy, public health reporting, regulated studies, accounts and billing, claims and reimbursement, patient administration and personnel management scheduling.

Starting from version 3 of the HL7 specifications (commonly referred to as HL7 V3), all HL7 messages and data structures are specified and implemented as hierarchically-structured eXtensible Markup Language (XML) documents. All data structures are derived, using a well-defined methodology, from a single Reference Information Model (RIM). The RIM provides an explicit representation of the semantic and lexical connections that exist between the information items carried in the fields of HL7 messages. Further details regarding the HL7 organization and specifications are available at www.hl7.org.

As part of the processing of HL7 messages in healthcare-related computer systems, it is often desired to store the information carried in HL7 messages and documents using a relational database management system (RDBMS). Exemplary RDBMSs include DB2® produced by IBM Corporation (Armonk, N.Y.), Oracle® produced by Oracle Corporation (Redwood Shores, Calif.) and Microsoft® Office Access produced by Microsoft Corporation (Redmond, Wash.). Information regarding these products can be found at www-306.ibm.com/software/data/db2/, www.oracle.com and www.office.microsoft.com, respectively.

Several methods are known in the art for converting object models and hierarchical data structures into relational database schemas, while preserving the structure and interrelationships between data items. For example, Ambler describes such methods in "Mapping Objects to Relational Databases," www-106.ibm.com/developerworks/webservices/library/ws-mapping-to-rdb, July 2000. Zhang and Dewey describe a method for converting an HL7 XML document type definition (DTD) into a relational database schema in "Electronic Medical Record Systems and Databases," icmit.mit.edu/sxzhang/healthcare/word.htm, May 2001.

In addition, several methods and systems for converting object models to relational schemas and for storing XML-structured documents in databases appear in the patent literature. For example, U.S. Pat. No. 6,529,909 describes a method and a system for translating an object attribute to and from a database value. U.S. Pat. No. 6,163,781 describes a system for storing a definitional data table that defines variable symbols representing respective measurable physical phenomena. The definitional data table uniquely defines the variable symbols by relating them to respective data domains for the respective phenomena represented by the symbols. An object-to-relational data converter is used to map object attributes into two relational tables stored in a memory. The system is used for processing, storing, and retrieving of healthcare-related information in very large database systems.

Methods for converting XML DTDs to relational database schemas are also described by Shanmugasundaram et al., in "Relational Databases for Querying XML Documents: Limitations and opportunities." Proceedings of the 25th Very Large Data Bases Conference (VLDB'99), Edinburgh, Scotland, September 1999, pages 302-314.

Some software tools for performing XML-database conversions are available. For example, SkyHawk Systems (San Jose, Calif.) produce a database middleware package called "Connect XML-2-DB" for transforming and moving data from XML documents to relational databases using mapping files. Another middleware package for transferring data between XML documents and relational databases, called "XML-DBMS," was developed by Robert Bourret (Felton, Calif.). This middleware package is available at www.rpbourret.com/xmldbms/.

SUMMARY OF THE INVENTION

There is therefore provided, in accordance with an embodiment of the present invention, a method for storing communication messages in a relational database, which includes accepting an object model including data elements and associations between the data elements, derived from a hierarchically-structured HL7 specification. A relational database is defined, representing the object model based on the data elements and the associations. Upon receiving a communication message including data items corresponding to one or more of the data elements, the message conforming to the HL7 specification, the data items are stored in the relational database so as to preserve the associations between the data items, as defined in the object model.

Apparatus for storing communication messages in a relational database and a computer software product for processing communication messages are also provided.

The present invention will be more fully understood from the following detailed description of the embodiments thereof, taken together with the drawings in which:

DETAILED DESCRIPTION OF EMBODIMENTS

Overview

Figure 1:
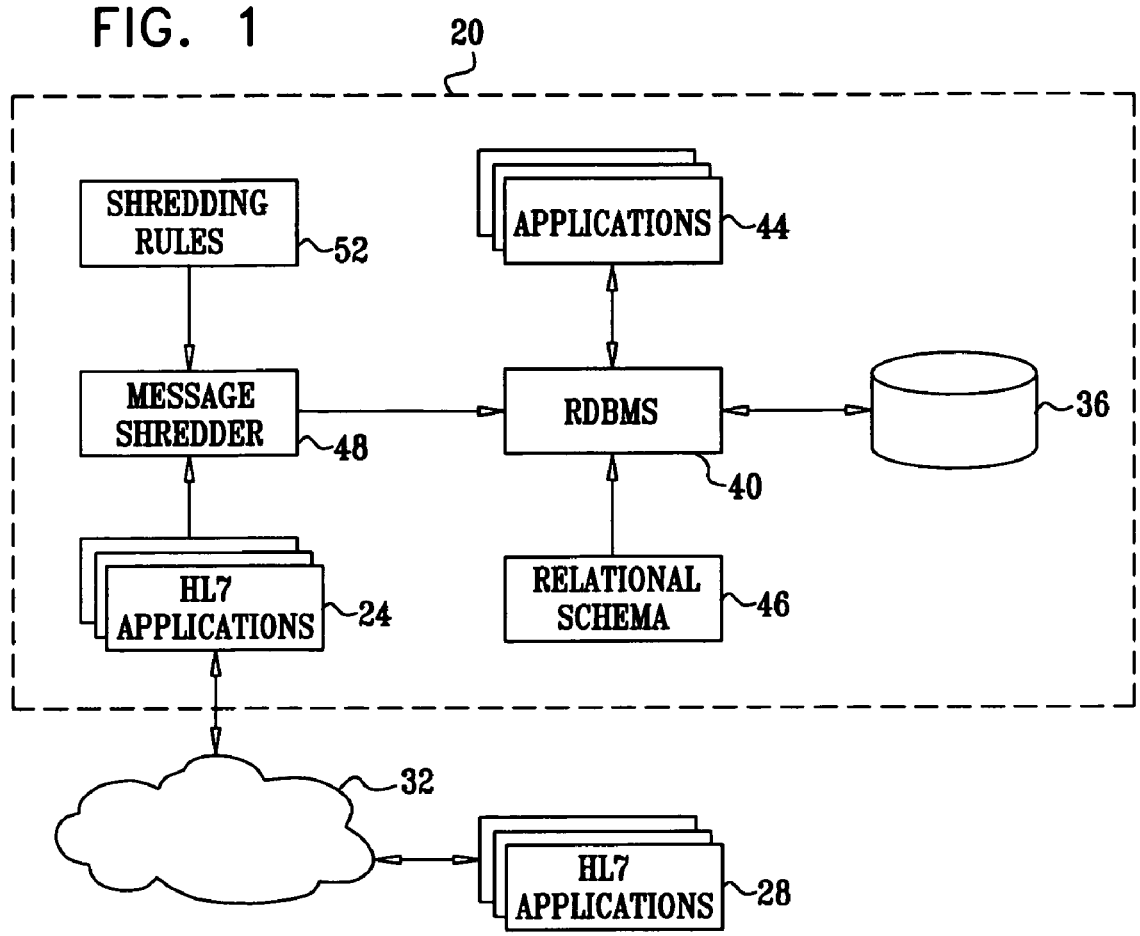
FIG. 1 is a block diagram that schematically illustrates a healthcare computer system, in accordance with an embodiment of the present invention.

In many healthcare-related applications, it is desirable to store hierarchically-structured HL7 messages and documents in a relational database. The database storage process should preserve the relationships between the different data items in the message, as defined in the HL7 specification.

All HL7 messages and documents for a particular healthcare domain are derived from a Refined Message Information Model (RMIM), using a methodology that will be described below. The RMIM comprises data elements called classes, and associations that define the relationships between classes, as relevant to the particular healthcare domain. Healthcare domains specified by HL7 specifications include, for example, Regulated Clinical Research Information Management (RCRIM), clinical genomics and medication.

Conventional methods for mapping XML structures or object models to relational databases do not provide a specialized mapping methodology for the HL7 V3 specifications. As will be demonstrated hereinbelow, designing a relational schema based on the RMIM object model is a non-trivial task, since the RMIM is typically a hierarchical model comprising recursive associations, complex non-fixed data types and elements with an unbounded number of sub-elements.

Embodiments of the present invention provide methods and systems for producing a relational schema based on an object model such as an RMIM, for a particular healthcare domain. Using the produced relational schema, HL7 messages and documents that comply with the object model can be stored in a relational database, while preserving the data items and the relationships between them.

The methods described below automatically create a table-based relational schema, in which multiple tables are associated with one another using shared attributes or keys. The produced relational schema is logically equivalent to the object model. In some embodiments, new class tables are automatically created, and the RMIM classes are mapped to these newly-created class tables in the relational schema. For some RMIM associations, new association tables are created, and the associations are mapped to the newly-created association tables. Other associations are accounted for by adding columns to existing class tables. The data types and attributes of the RMIM are mapped to newly-defined or existing data types in the relational schema. In some cases, data type tables and attribute tables are also created for some of the RMIM data types and attributes. The methods described below also account for recursive associations and for several types of associations between multiple classes, as will be explained below.

In some embodiments, given an RMIM of a HL7 V3 specification, the method for generating a relational database comprises the following steps:

1. Creating new relational database data types for a global entity identifier, a local entity identifier, an auxiliary data type, and an element name data type.

2. Mapping simple HL7 data types to new relational database distinct types and compound HL7 data types to relational tables.

3. Mapping RMIM classes to corresponding class tables.

4. Mapping RMIM 1:n associations to corresponding columns and n:m associations to corresponding association tables.

5. Replacing distinct data types with the corresponding built-in database data types.

In some embodiments, the disclosed methods and systems apply knowledge of the specific healthcare domain into the mapping process. Domain-specific information is applied, for example, by assigning the global entity, local entity and auxiliary fragments, and using these assignments in the mapping process. Additionally, some embodiments provide a systematic and extensible method of choosing, capturing and using the appropriate domain knowledge.

In some embodiments, a set of shredding rules is produced in parallel to the generation of the relational schema. At runtime, incoming communication messages that comply with the object model are parsed and shredded in accordance with the shredding rules. Data items are extracted from these communication messages and stored in the relational database, in accordance with the relational schema.

The methods described below are typically applicable to all HL7 V3 standards, since the input to the method is the RMIM object model, which is an artifact of every HL7 V3 standard.

System Description

FIG. 1 is a block diagram that schematically illustrates a healthcare computer system 20, in accordance with an embodiment of the present invention. System 20 comprises one or more healthcare-related applications 24 (referred to as "HL7 applications") that communicate with each other using HL7 messages. In some embodiments, applications 24 also communicate with external HL7 applications 28 using HL7 messages over a wide area network (WAN) 32, typically the Internet.

The HL7 specification defines both messages and documents. Such messages and documents are exchanged, stored and otherwise processed by the HL7 applications. In the context of the present patent application and in the claims, the term "HL7 message" refers to both communication messages and documents defined by the HL7 specifications. Furthermore, the methods and systems described herein process hierarchically-structured HL7 messages, such as XML-structured messages. Therefore, the term "HL7 specification" refers to any HL7 specification that defines hierarchically-structured information, typically comprising the HL7 V3 specifications cited above and anticipated later versions.

As part of the processing of healthcare-related information by applications 24, incoming communication messages that comply with the HL7 specification are stored in a relational database (RDB) 36, typically using an RDBMS 40. The RDB and RDBMS may reside on any suitable storage devices and any suitable management system that support a relational model, as are known in the art. Typically, RDBMS 40 runs on a suitable database processor, such as a general-purpose computer with appropriate software. In some embodiments, the RDB may also be accessed by other, non-HL7 applications 44 in system 20.

RDBMS 40 stores the data items of the incoming HL7 messages in RDB 36 in accordance with a relational schema 46. The relational schema defines a relational data model for RDBMS 40. In order to process the messages correctly and without loss of information, the data model should correspond to the relevant HL7 specification, to which the HL7 messages comply. In other words, the definitions of data items and the associations between data items, as defined in the HL7 specification, should be preserved when storing the data items in the RDB in accordance with the relational schema. Methods for automatically generating relational schema 46 based on the HL7 specification are described below.

As mentioned above, HL7 messages are represented in terms of hierarchically-structured XML instances. In order to store an HL7 message in the RDB, the XML instance is shredded into separate data items by a message shredder 48, to be stored in the different tables of RDB 36. Shredder 48 shreds the HL7 messages in accordance with a set of shredding rules 52. The rules are generated using methods which will be described below. The shredded messages are provided to RDBMS 40 for storing in RDB 36, in accordance with relational schema 46. In some embodiments, shredder 48 comprises an off-the-shelf message shredder. An exemplary shredder is the DB2 XML Extender produced by IBM. Details regarding this product are available at www-306.ibm.com/software/data/db2/extenders/xmlext.

In general, HL7 V3 specifications are reductions or specializations of the RIM to address the needs of specific usages in the healthcare industry. For example, the Clinical Document Architecture (CDA) is a specification for producing and exchanging clinical documents, derived from the HL7 RIM, in a standard, XML-based structure. Further details of the CDA specifications can be found in a publication by Dolin, et al. entitled "HL7 Clinical Document Architecture, Release 2, Committee Ballot #02," Dec. 8, 2003, published by the HL7 Structured Documents Technical Committee. The CDA specification documentation is also available at http://www.hl7.org/v3ballot/html/infrastructure/cda/cda.h tm. Other specifications derived from the RIM cover Regulated Clinical Research Information Management (RCRIM), Clinical-Genomics, Medication, etc. Although many of the examples given throughout this patent application refer to the CDA specification, this specification is used purely by way of example. The methods and systems described herein can be used to generate a relational schema from any suitable HL7 reduced specification.

The HL7 V3 specification cited above defines a methodology for deriving such reduced specifications based on the generic RIM. Using the defined methodology, a Refined Message Information Model (RMIM) is first created. (The RMIM is sometimes referred to as a Domain Information Model, or DIM.) The RMIM is an object model, typically presented using Microsoft Visio® and obtained by applying clones and constraints on the RIM. The RMIM comprises classes, typically represented as rectangles, and associations between classes, typically denoted by arrows. A notation similar to Unified Modeling Language (UML) model is often used to represent the RMIM. (Details regarding UML can be found at http://www.uml.org/.) Each RMIM class and association may comprise one or more attributes, in accordance with pre-defined data types. Producing the RMIM is the main task of the authors and modelers of the HL7 specifications, which requires expertise in the relevant domain and extensive reviews to make sure all relevant use cases are covered.

After producing the RMIM for the relevant domain, a Hierarchical Message Description (HMD) is produced, often using an automatic conversion tool. The HMD is typically a spreadsheet that describes the meta-information of the specification in question. Finally, another automatic tool transforms the HMD into an XML schema that represents the reduced specification. HL7 messages that comply with the specification are XML instances that comply with the XML schema. These messages can thus be parsed using the XML schema.

Figure 2:
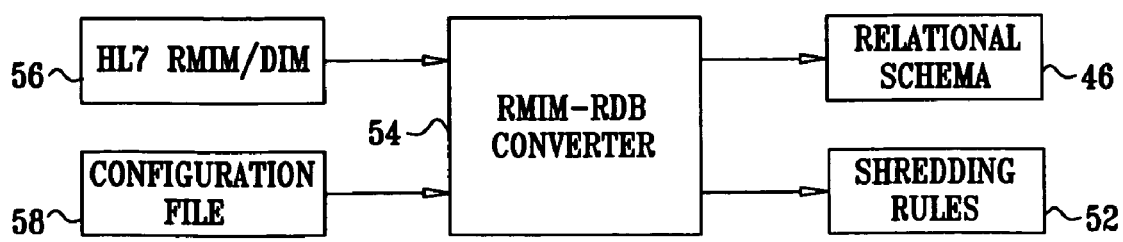
FIG. 2 is a block diagram that schematically illustrates a system for converting an HL7 RMIM to a relational schema, in accordance with an embodiment of the present invention.

FIG. 2 is a block diagram that schematically illustrates a system for converting an HL7 RMIM to a relational schema, in accordance with an embodiment of the present invention. An RMIM-RDB converter 54 accepts an HL7 RMIM 56, or an equivalent UML model, which defines an object model for the relevant domain. The RMIM-RDB converter also accepts configuration definitions, typically in the form of a configuration file 58, comprising definitions of entities and data types to be used in the conversion process, as will be described below.

The RMIM-RDB converter 54 processes RMIM 56, using methods which will be described below, to produce relational schema 46. In some embodiments, converter 54 produces scripts, such as Data Definition Language (DDL) scripts, that describe the relational schema. (DDL is described, for example, by Chamberlin in "A Complete Guide to DB2 Universal Database," Morgan Kaufmann, first edition, August 1998.)

In some embodiments, converter 54 also produces a set of shredding rules 52. The shredding rules define how an HL7 message (represented as an XML instance), which is compliant with the reduced HL7 specification, is to be shredded into the RDB defined by relational schema 46. In some embodiments, converter 54 produces scripts that perform the shredding process. In some embodiments, incoming HL7 messages are parsed and shredded at runtime by message shredder 48 in accordance with shredding rules 52. Data items are extracted from these messages and stored in RDB 36 in accordance with relational schema 46. Typically, relational schema 46 and shredding rules 52 are updated whenever changes are made to RMIM 56.

Typically, RMIM-RDB converter 54 comprises a general-purpose computer, which is programmed in software to carry out the functions described herein. The software may be downloaded to the computer in electronic form, over a network, for example, or it may alternatively be supplied to the computer on tangible media, such as CD-ROM. Further alternatively, converter 54 may be implemented using a combination of hardware and software elements. The RMIM-RDB converter may comprise a standalone unit, or may alternatively be integrated with other computing platforms of system 20.

Figure 3:
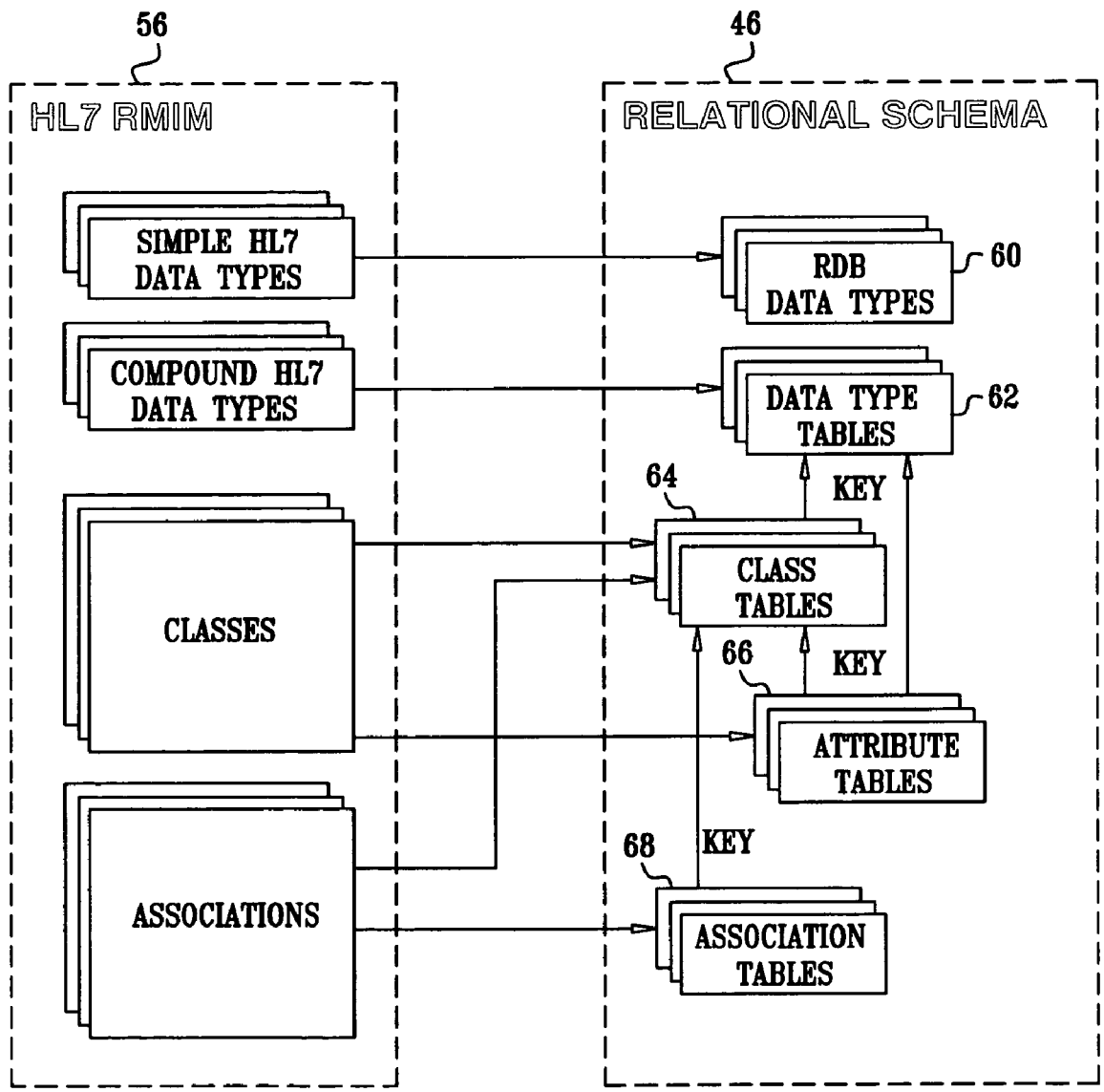
FIG. 3 is a diagram that schematically illustrates elements of an HL7 RMIM and of a relational schema, in accordance with an embodiment of the present invention.

FIG. 3 is a diagram that schematically illustrates elements of HL7 RMIM 56 and the mapping of these elements to objects in relational schema 46, in accordance with an embodiment of the present invention. A method for converting an HL7 RMIM to a relational schema is shown in detail in FIG. 4 below.

As described above, RMIM 56 is an object model that defines the different data items and associations between data items, as relevant to the reduced HL7 specification. The RMIM comprises classes that correspond to various healthcare-related entities, such as documents, facilities and persons. The relationships between classes are represented using associations. Both classes and associations have attributes, which conform to specified HL7 data types. Data types can be either simple or compound. A simple HL7 data type corresponds to a single field or element, such as a string or a numerical value. A compound HL7 data type has two or more attributes, which may themselves be simple or compound.

Relational schemas, as known in the art, represent data in terms of multiple tables that are logically associated with each other using shared attributes. The shared attributes are referred to as keys. The methods described below produce a relational schema that preserves the logical structure of the RMIM and transforms it to the table-based structure of the relational database.

As will be shown below, the simple HL7 data types in the RMIM are mapped to corresponding RDB data types 60 in relational schema 46. The compound HL7 data types are mapped to data type tables 62. The RMIM classes are mapped to class tables 64. Some RMIM class attributes are mapped to columns in existing class tables 64, while other class attributes are mapped to attribute tables 66, as will be explained in detail below. Similarly, some RMIM associations are mapped to columns in existing class tables 64, while other associations are mapped to association tables 68.

The different tables in relational schema 46 are associated with each other using keys, indicated by arrows in FIG. 3. The keys are represented in terms of dedicated columns in the various tables of the relational schema. By using the keys, the relational schema preserves the logical connections between data items, as defined in the RMIM.

Conversion Method Description

Figure 4:
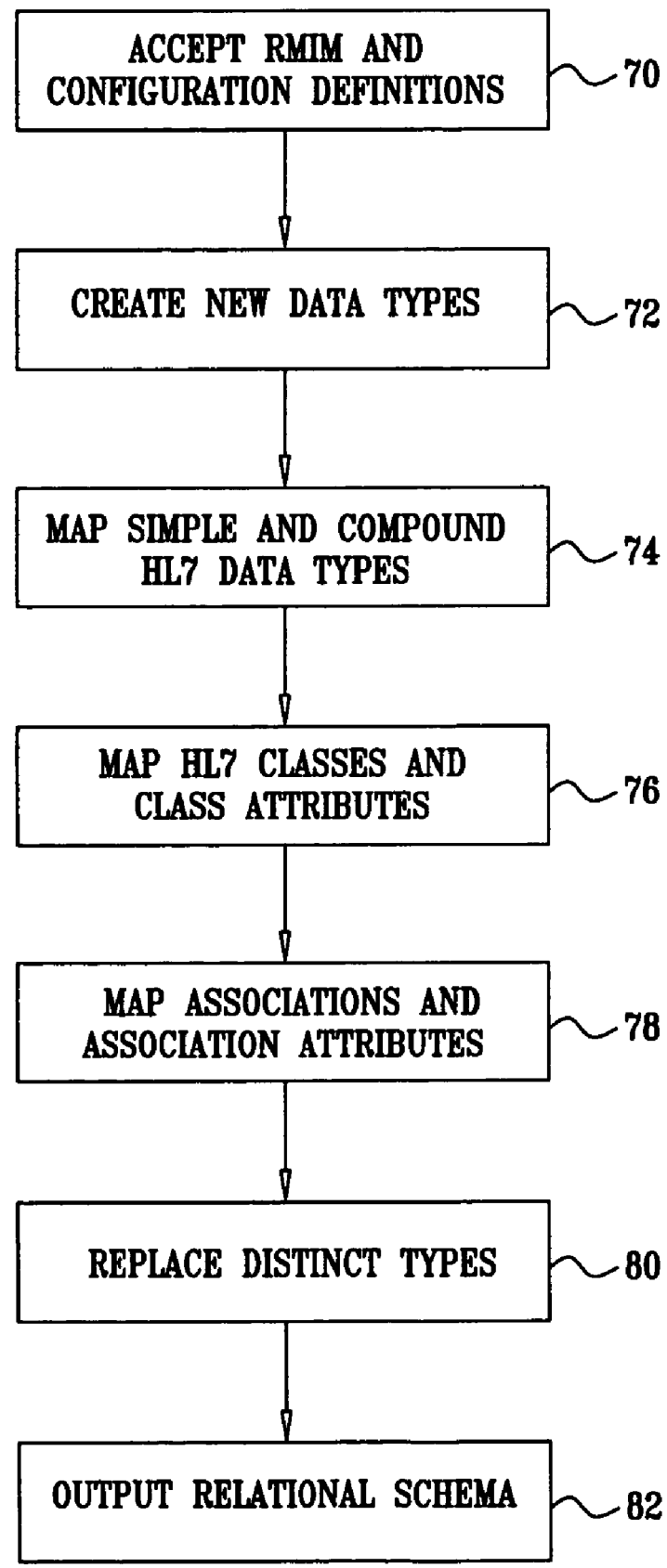
FIG. 4 is a flow chart that schematically illustrates a method for converting an HL7 specification to a relational schema, in accordance with an embodiment of the present invention.

FIG. 4 is a flow chart that schematically illustrates a method for converting an HL7 specification into a relational schema, carried out by RMIM-RDB converter 54 in accordance with an embodiment of the present invention. The method begins with converter 54 accepting RMIM 56 and configuration file 58, at an input step 70. As mentioned above, the RMIM is typically provided as an equivalent UML model.

Configuration file 58 typically comprises information that is derived from knowledge of the specific healthcare domain and is not explicitly defined in the RMIM. For example, for each class in the RMIM, the configuration file defines whether the class is a global entity (a class that is shared by multiple HL7 messages, such as Patient, Facility and Code) or a local entity (a class that is only relevant to a specific HL7 message, such as an Observation described by a specific document). The configuration file may also comprise definitions of the cardinality of associations between classes, as will be explained below.

In some embodiments, when the RMIM is represented as a UML model, semantic information that describes domain-specific knowledge can be augmented onto the model using a UML Profile, instead of providing it in the configuration file. Such domain knowledge may comprise, for example, assigning classes as global entities or local entities, assigning auxiliary fragments, and identifying which attributes of a compound HL7 data type comprise the primary key.

Converter 54 defines four new data types in the relational schema, at a data type definition step 72. The following new data types are defined:

A data type for the unique identifier of a global entity. This data type will later be used to represent keys for querying database class tables 64 that correspond to global entities, as will be explained in detail below. For example, the following DDL excerpt defines a data type called CDA.KEY_ID:
CREATE DISTINCT TYPE CDA.KEY_ID AS VARCHAR(64) WITH COMPARISONS;
COMMENT ON DISTINCT TYPE CDA.KEY_ID IS 'The type for IDs that are unique over all documents';
(The DDL examples given throughout this patent application are taken from an embodiment that uses DB2 as the RDBMS. Although the examples are written using DB2 syntax, the features and functionality of these examples can also be implemented using other suitable RDBMSs in a similar manner.)

A data type for the unique identifier of a local entity. This data type will later be used as a key for querying class tables 64 that correspond to local entities. For example, the following DDL excerpt defines a data type called CDA.INDOC_ID:
CREATE DISTINCT TYPE CDA.INDOC_ID AS VARCHAR(32) WITH COMPARISONS;
COMMENT ON DISTINCT TYPE CDA.INDOC_ID IS 'The type for IDs that are unique within a document';

An auxiliary (AUX) data type. When shredding an HL7 message, it is sometimes desirable to store an entire XML fragment (i.e., part of an XML document, which does not necessarily have a single root) in a single column without shredding it. The AUX data type is used in such cases. For example, CDA documents often contain free text elements. It is sometimes desirable not to shred such elements and store the entire text, with the associated formatting and styling markup, as a single attribute. Specifically, the element "text" in the CDA specification comprises rendering guidelines and formatting-related sub-elements such as <table>, and <li>. The AUX data type is typically used to define a column that stores the entire text element (XML fragment). The following exemplary DDL excerpt defines a data type called CDA.AUX:
CREATE DISTINCT TYPE CDA.AUX AS CLOB (10K);
COMMENT ON DISTINCT TYPE CDA.AUX IS 'The type for XML fragments';

An element name data type. The RMIM occasionally comprises a choice between several objects (classes or associations), as will be demonstrated below. In order to handle such multiple XML elements, it is desirable to attach a unique name to each element. The element name data type is used for this purpose. The following exemplary DDL excerpt defines a data type called CDA.ELEMENT_NAME:
CREATE DISTINCT TYPE CDA.ELEMENT_NAME AS VARCHAR(32) WITH COMPARISONS;
COMMENT ON DISTINCT TYPE CDA.ELEMENT_NAME IS 'The type for the name of an XML element, e.g., StructuedBody, Section;

Converter 54 then maps HL7 data types to RDB data types 60, at a data type mapping step 74. Converter 54 maps each HL7 data type that appears in the RMIM to an appropriate RDB data type 60, which is defined in the RDBMS being used.

Class attributes occasionally have constraints defined over their data types. In some embodiments, message shredder 48 validates each incoming HL7 message against its XML schema prior to shredding. Therefore, converter 54 typically ignores the data type constraints.

In some embodiments, converter 54 defines an appropriate distinct type for each simple HL7 data type in the RMIM. A distinct type is a user-defined alias of a built-in RDB data type 60. In some embodiments, converter 54 defines distinct types, whose names resemble the corresponding HL7 data types. Although this type of definition is not mandatory, it is sometimes desirable in order to make the relational schema more readable to users who are familiar with the HL7 data type names. For example, the following DDL code defines four distinct types called CDA.BL, CDA.ST, CDA.ED, and CDA.TS that correspond to the simple HL7 data types BL, ST, ED, and TS, respectively:
CREATE DISTINCT TYPE CDA.BL AS VARCHAR(5) WITH COMPARISONS;
COMMENT ON DISTINCT TYPE CDA.BL IS 'The HL7 Boolean (BL) type stands for the values of two-valued logic. A Boolean value can be either TRUE or FALSE, or, as any other value may be NULL.';

CREATE DISTINCT TYPE CDA.ST AS VARCHAR(32) WITH COMPARISONS;
COMMENT ON DISTINCT TYPE CDA.ST IS 'The HL7 Character String (ST) type stands for text data used for names, symbols, and formal expressions.';
CREATE DISTINCT TYPE CDA.ED AS CLOB(10K);
COMMENT ON DISTINCT TYPE CDA.ED IS 'The HL7 Encapsulated Data (ED) type stands for unformatted or formatted written language, multimedia data, or structured information as defined by a different standard (e.g., XML-signatures).';
CREATE DISTINCT TYPE CDA.TS AS TIMESTAMP WITH COMPARISONS;
COMMENT ON DISTINCT TYPE CDA.TS IS 'The HL7 Point In Time (TS) type stands for a quantity specifying a point on the axis of natural time';

In addition to the simple data types, the RMIM also comprises compound HL7 data types. For each compound HL7 data type in the RMIM, converter 54 defines a data type table 62 in the relational schema. The columns of the data type table correspond to the attributes of the compound data type. Converter 54 adds an additional column to the data type table, corresponding to a KEY_ID type attribute, as defined above. The KEY_ID column stores a primary key for querying data type table 62. The key definition is determined specifically for each data type table 62, so as to enable unique addressing. In some embodiments, the information as to which attribute (or combination of attributes) defines the primary key is provided in configuration file 58.

In some embodiments, the name given to the data type table corresponds to the semantic use of the compound data type. In these embodiments, if a certain compound HL7 data type has several semantic uses, several data type tables 62 will be defined.

One exception in this method is the "II" compound HL7 data type, which represents unique identifiers. Converter 54 does not define a table for this data type, as unique identifiers are typically a part of the tables they specify.

The following DDL code shows an exemplary data type table definition, corresponding to the compound HL7 data type CE ("Coded with Equivalents"), used in this example to store a language code:

```
CREATE TABLE CDA.LANG_CODE
(
    KEY_ID              CDA.KEY_ID NOT NULL,
    CODE                CDA.CS,
    CODE_SYSTEM         CDA.UID,
    CODE_SYSTEM_NAME    CDA.ST,
    CODE_SYSTEM_VERSION CDA.ST,
    DISPLAY_NAME        CDA.LONG_ST,
    TRANSLATION         CDA.AUX,
    PRIMARY KEY (KEY_ID)
);
```

Having defined and mapped the various data types, converter 54 maps the HL7 classes to tables in the relational schema, at a class mapping step 76. For each class in the RMIM, converter 54 defines a corresponding class table 64 in the relational schema.

For classes that are defined as global entities, converter 54 adds to the class table a column of type KEY_ID that holds the primary key to the class table. For classes that are defined as local entities, converter 54 adds two columns that hold two separate identifiers, namely a document identifier and a local identifier. The document identifier is unique over all HL7 messages and documents. The local identifier (denoted INDOC_ID) is unique over all entities in the specific HL7 message. As a result, the two columns jointly form the primary key of the class table.

The other columns of the class table are defined by converter 54, so as to correspond to the attributes of the RMIM class in the following manner:

Each attribute that corresponds to a simple HL7 data type is mapped to a single column of the class table.

For attributes that correspond to compound HL7 data types, converter 54 creates a column that holds the key of the data type table associated with the relevant compound HL7 data type, and adds an appropriate "foreign key" statement to the class table definition.

Some HL7 class attributes are defined as having "cardinality n." An attribute of cardinality n may appear zero or more times within its class. The number of appearances of the attribute is not fixed, and may vary from one HL7 message to another. The actual number of appearances is revealed to the message shredder only at runtime, when a specific XML instance (HL7 message) is received for processing. Attributes of cardinality n are mapped in the following manner:

For each attribute of cardinality n that corresponds to a simple HL7 data type, converter 54 creates a corresponding attribute table 66, whose columns hold the key to (in other words—point to) the relevant class table 64 plus a column for the actual attribute value. At runtime, the shredding process will create an attribute table having n rows, one row per each appearance of the attribute.

For each attribute of cardinality n that corresponds to a compound HL7 data type, converter 54 creates an attribute table 66, whose columns hold the keys to the class table and to the data type table of the relevant compound data type.

Some RMIM class attributes correspond to a data type denoted ANY. The actual data type for such attributes may vary from one HL7 message to another, and is revealed to the message shredder only at runtime, when a particular HL7 message (XML instance) arrives. For each attribute in the class that is of type ANY, converter 54 adds to the class table a column that holds the name of the type (using the element name data type defined above) and a column that holds either the actual data or a key to the relevant data type table. For example, the HL7 data type for the attribute value of class Observation is ANY. When mapping this attribute, converter 54 adds two columns named VALUE and VALUE_TYPE to the class table of the Observation class. The column VALUE_TYPE holds the actual HL7 data type of the value field such as CV, CD or ST. The column VALUE holds either the actual data, if the type in VALUE_TYPE is a simple HL7 data type. If the type in VALUE_TYPE is a compound data type, column VALUE contains a key to the data type table associated with this compound HL7 data type.

In some cases, an attribute may have a fixed value assigned to it. When defining the columns of the class table, the converter typically ignores such fixed value attributes.

The following two examples demonstrate the process of creating a class table from an RMIM class definition. The first example refers to a global entity class, whereas the second example refers to a local entity. The first example demonstrates the creation of a class table for the ClinicalDocument class, which is the root class of the HL7 CDA RMIM. The following class definition is an extract from the CDA RMIM:

ClinicalDocument
classCode*: <=DOCCLIN
moodCode*: <=EVN
id:SET <II>[1 ... 1]

code: CE CWE [1 . . . 1]<=DocumentType
title: ST [0 . . . 1]
effectiveTime: TS [1 . . . 1]
confidentialityCode: CE CWE [0 . . . 1]
<=x_BasicConfidentialityKind "N"
languagecode: CS CNE [0 . . . 1]<=HumanLanguage
setid: II [0 . . . 1]
versionNumber: INT [0 . . . 1]
copyTime: TS [0 . . . 1]

Each line in the RMIM class definition describes a class attribute. Values inside square brackets indicate the cardinality of the attribute. (For example, [0 . . . 1] indicates that the attribute may appear between zero and one times in each class instance. Attributes of cardinality n are marked with [0 . . . *].) For attributes that correspond to compound data types, the class definition points to the appropriate data type definition. See, for example, the attribute languagecode that corresponds to the compound data type CS. In this example, classCode and moodcode are fixed value attributes.

The following DDL code is the class table definition that corresponds to the class definition above, as extracted from the relational schema produced by converter 54:

```
CREATE TABLE CDA.CLINICAL_DOCUMENT
(
    KEY_ID                      CDA.KEY_ID NOT NULL,
    ID_ROOT                     CDA.UID,
    ID_EXTENSION                CDA.ST,
    ID_VALID_TIME               CDA.TS,
    CODE_KEY_ID                 CDA.KEY_ID,
    TITLE                       CDA.ST,
    EFFECTIVE_TIME              CDA.TS,
    CONFIDENTIALITY_CODE_KEY_ID CDA.KEY_ID,
    LANGUAGE_CODE_KEY_ID        CDA.KEY_ID,
    SET_ID_ROOT                 CDA.UID,
    SET_ID_EXTENSION            CDA.ST,
    SET_ID_VALID_TIME           CDA.TS,
    VERSION_NUMBER              INTEGER,
    COPY_TIME                   CDA.TS,
    PRIMARY KEY (KEY_ID),
    FOREIGN KEY (CODE_KEY_ID ) REFERENCES
CDA.CODE(KEY_ID) ON DELETE SET NULL,
FOREIGN KEY (CONFIDENTIALITY_CODE_KEY_ID )
REFERENCES CDA.CONFIDENTIALITY_CODE(KEY_ID) ON
DELETE SET NULL,
FOREIGN KEY (LANGUAGE_CODE_KEY_ID) REFERENCES
CDA.LANG_CODE(KEY_ID) ON DELETE SET NULL
)
```

The different mapping rules defined above can be seen in the example. For example, the attribute effectiveTime in the RMIM, which corresponds to a simple HL7 data type, was mapped to the column EFFECTIVE_TIME in the class table definition. The attribute languagecode, which corresponds to a compound data type, was mapped to LANGUAGE_CODE_KEY_ID in the class table, with the appropriate FOREIGN KEY statement added at the bottom of the table definition.

The second example demonstrates the creation of a class table for the Section class, which is defined as a local entity in the HL7 CDA RMIM. The following class definition is an extract from the CDA RMIM:
Section
classCode*: <=DOCSECT
moodCode*: <=EVN
id: SET <II>[0 . . . 1]
code: CE CWE [0 . . . 1]<=DocumentSectionType
text: ED [0 . . . 1]
title: ST [0 . . . 1]
confidentialityCode: SET<CE>CWE [0 . . . 1]
<=x_BasicConfidentialityKind
languageCode: CS CNE [0 . . . 1]<=HumanLanguage The following DDL code is the class table definition that corresponds to the Section class definition above, as extracted from the relational schema produced by converter 54:

```
CREATE TABLE CDA.SECTION
(
    INDOC_ID                    CDA.INDOC_ID NOT NULL,
    CLINICAL_DOCUMENT_KEY_ID    CDA.KEY_ID NOT NULL,
    ID_ROOT                     CDA.UID,
    ID_EXTENSION                CDA.MID_ST,
    ID_VALID_TIME               CDA.TS,
    CODE_KEY_ID                 CDA.KEY_ID,
    TEXT                        CDA.ED,
    TITLE                       CDA.LONG_ST,
    CONFIDENTIALITY_CODE_KEY_ID CDA.KEY_ID,
    LANGUAGE_CODE_KEY_ID        CDA.KEY_ID,
    PRIMARY KEY (INDOC_ID,
CLINICAL_DOCUMENT_KEY_ID),
    FOREIGN KEY (CLINICAL_DOCUMENT_KEY_ID)
REFERENCES CDA.CLINICAL_DOCUMENT(KEY_ID) ON
DELETE CASCADE ON UPDATE RESTRICT,
    FOREIGN KEY (CODE_KEY_ID ) REFERENCES
CDA.CODE(KEY_ID) ON DELETE SET NULL,
    FOREIGN KEY (CONFIDENTIALITY_CODE_KEY_ID )
REFERENCES CDA.CONFIDENTIALITY_CODE(KEY_ID) ON
DELETE SET NULL,
    FOREIGN KEY (LANGUAGE_CODE_KEY_ID)
REFERENCES CDA.LANG_CODE(KEY_ID) ON DELETE SET NULL
);
```

The example above demonstrates some of the mapping rules that are relevant to class tables for local entities. For example, the two columns INDOC_ID and CLINICAL_DOCUMENT_KEY_ID are jointly used as the primary key to the class table. Note the appropriate PRIMARY KEY statement added at the bottom of the table definition.

Having mapped the classes and the class attributes, converter 54 now maps the associations and the association attributes, at an association mapping step 78. An RMIM association in the HL7 RMIM is a definition of a relationship between classes. An association typically comprises association attributes, which can be of simple HL7 data type or compound HL7 data type.

Associations can have 1:n on n:m cardinalities. For example, the Authenticator association has n:m cardinality, since a document may be authenticated by several physicians and a physician may authenticate several different documents. The LegalAuthenticator association, on the other hand, has 1:n cardinality since a document can only have one legal authenticator. For an association of cardinality 1:n, the class having cardinality 1 (LegalAuthenticator in our example) is regarded as the parent class and the class having cardinality n (ClinicalDocument in our example) is regarded as the child class.

Typically, n:m cardinalities are not shown explicitly in the RMIM since the RMIM comprises an object model of a single HL7 message and does not normally deal with relationships of multiple messages. Therefore, in some embodiments the classification of a particular association as having cardinality n:m is typically given in configuration file 58.

For each association of cardinality 1:n, converter 54 adds columns to the class table of the child class. The added columns hold the key to the class table of the parent class, and the association attributes that appear in the association definition in the RMIM. Similarly to class attributes, fixed value attributes are typically ignored.

Figure 5:
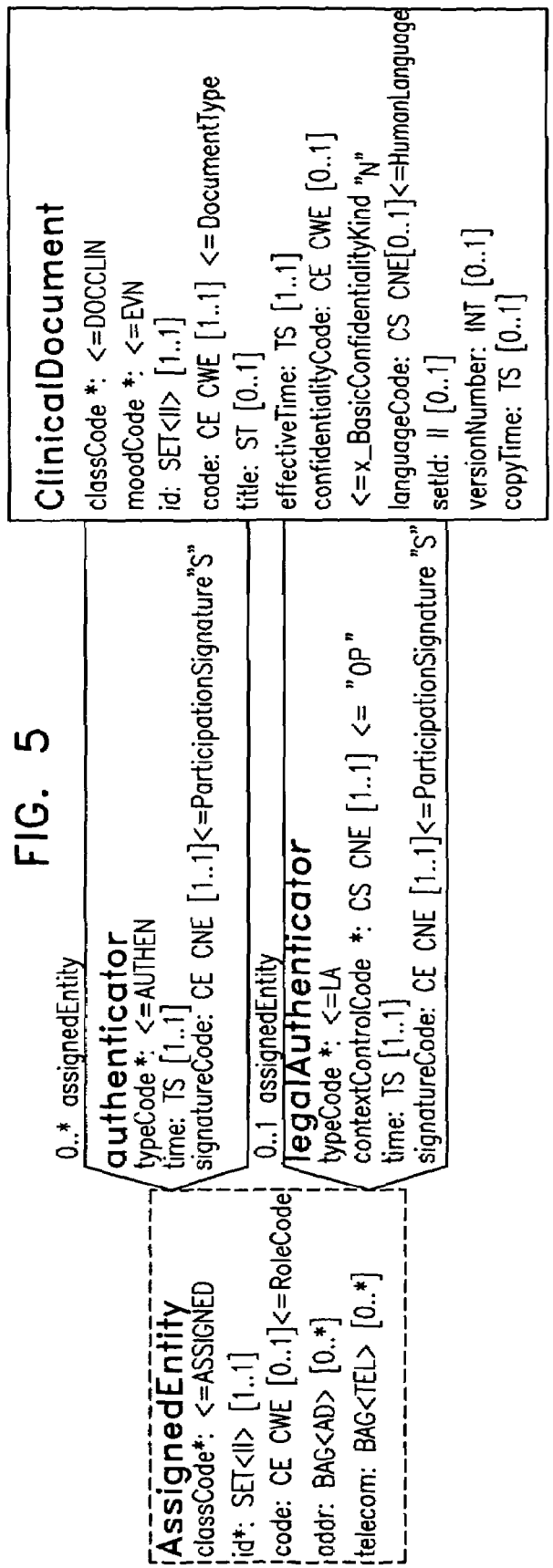
FIGS. 5 and 6 are diagrams that schematically illustrate parts of an HL7 RMIM, in accordance with an embodiment of the present invention.

For each association of cardinality n:m, converter 54 creates an association table, whose columns hold the keys to all class tables of the classes included in the association, as well as the association attributes. The primary key of the association table comprises the combined keys of the classes connected to the association. Converter 54 adds appropriate foreign key statements to the table definition. FIG. 5 below demonstrates the mapping of associations having cardinalities 1:n and n:m.

FIG. 5 is a diagram that schematically illustrates parts of the HL7 CDA RMIM, in accordance with an embodiment of the present invention. In this example, the ClinicalDocument class is associated with the AssignedEntity class using two different associations, namely Authenticator and LegalAuthenticator.

The LegalAuthenticator association has cardinality 1:n. Therefore, with regards to this association ClinicalDocument is regarded as the child class and AssignedEntity is regarded as the parent class. When mapping the LegalAuthenticator association, converter 54 adds its key and its association attributes to the CDA.CLINICAL_DOCUMENT class table created at class mapping step 76 above. The Authenticator association has cardinality n:m, as indicated in configuration file 58. Therefore, converter 54 creates an association table named CDA.AUTHENTICATOR, as described by the following DDL code. Note that the primary key definition includes both CLINICAL_DOCUMENT_KEY_ID and ASSIGNED_ENTITY_KEY_ID, as explained above:

```
CREATE TABLE CDA.AUTHENTICATOR
(
    CLINICAL_DOCUMENT_KEY_ID        CDA.KEY_ID,
    ASSIGNED_ENTITY_KEY_ID          CDA.KEY_ID,
    TIME_AUTHENTICATED              CDA.TS,
    SIGNATURE_CODE_KEY_ID           CDA.KEY_ID,
    PRIMARY KEY (CLINICAL_DOCUMENT_KEY_ID,
    ASSIGNED_ENTITY_KEY_ID),
    FOREIGN KEY (ASSIGNED_ENTITY_KEY_ID)
    REFERENCES CDA.ASSIGNED_ENTITY(KEY_ID) ON
    DELETE CASCADE ON UPDATE RESTRICT,
    FOREIGN KEY (CLINICAL_DOCUMENT_KEY_ID)
    REFERENCES CDA.CLINICAL_DOCUMENT(KEY_ID)
    ON DELETE CASCADE ON UPDATE RESTRICT,
    FOREIGN KEY (SIGNATURE_CODE_KEY_ID)
    REFERENCES CDA.CODE(KEY_ID) ON DELETE
    CASCADE ON UPDATE RESTRICT
);
```

In some cases, there may be several associations between the same two classes. In such cases, converter 54 adds to the class table of this class a column for each association. The added columns hold the names (XML elements) of the associations.

The HL7 RMIM allows for several classes to be grouped together to form a "choice of elements." This group of classes (referred to as a "group association") can be connected to other classes via associations. The actual class of the "group associations" may vary from one HL7 message to another, and is revealed to the message shredder only at runtime. In such cases, converter 54 adds to the class table a column that holds the name of the actual parent class as well as columns to hold the key of the actual parent class.

The HL7 RMIM also defined "hidden associations," typically of cardinality 1:n. In some embodiments, hidden associations are treated in a similar manner to ordinary associations by converter 54.

Figure 6:
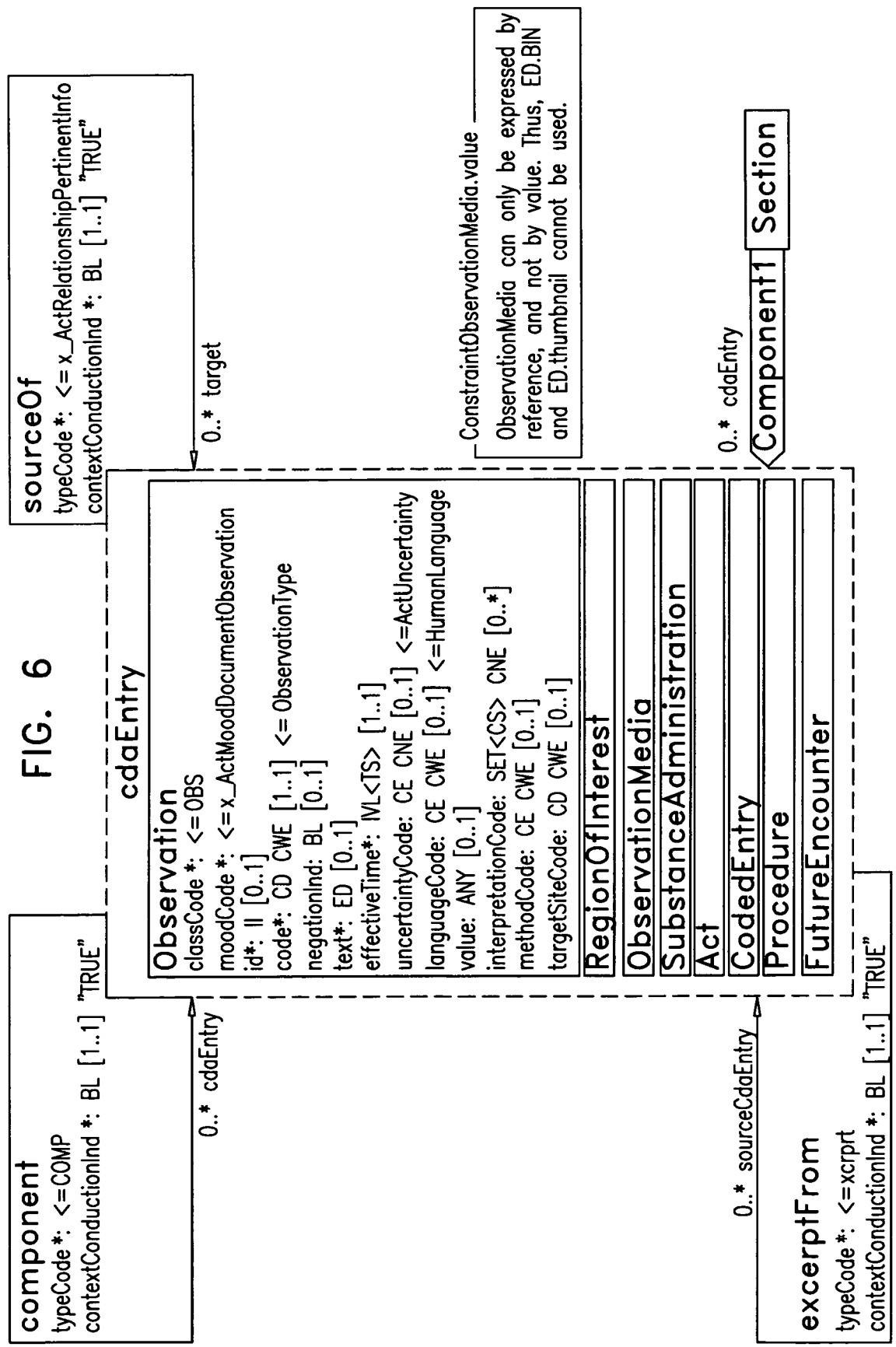

FIG. 6 is a diagram that schematically illustrates parts of an HL7 RMIM, in accordance with an embodiment of the present invention. The figure shows an additional example, extracted from the HL7 CDA RMIM, which demonstrates additional aspects of association mapping, as part of the implementation of association mapping step 78 of FIG. 4. The figure shows the Observation class as part of a group of classes named cdaEntry. cdaEntry comprises several additional classes (not shown). The grouping of the classes is shown as a dashed line in the figure. Two associations named component and sourceOf are shown. These associations are recursive, i.e., relating a class (or a group of classes, in this example) to itself.

Following class mapping step 76 and association mapping step 78, the class table of the Observation class is given by the following DDL code:

OBSERVATION Table
This is the table for Observation which is a local entity class.
OWNER_TYPE is either SECTION or Observation or RegionOfInterest or ObservationMedia or SubstanceAdministration or Act or CodedEntry or Procedure or FutureEncounter.
OWNER_ASSOCIATION_TYPE is either component or sourceOf or ExcerptFrom.
The CDA Observation is a clone of the RIM Observation class, used for representing coded and other observations.

```
CREATE TABLE CDA.OBSERVATION
(
    INDOC_ID                        CDA.INDOC_ID NOT NULL,
    CLINICAL_DOCUMENT_KEY_ID        CDA.KEY_ID NOT NULL,
    MOOD_CODE                       CDA.ST,
    ID_ROOT                         CDA.UID,
    ID_EXTENSION                    CDA.MID_ST,
    ID_VALID_TIME                   CDA.TS,
    CODE_KEY_ID                     CDA.KEY_ID,
    NEGATION_IND                    CDA.BL,
    TEXT                            CDA.ED,
    EFFECTIVE_TIME                  CDA.TS,
    UNCERTAINTY_CODE_KEY_ID         CDA.KEY_ID,
    LANGUAGE_CODE_KEY_ID            CDA.KEY_ID,
    VALUE_TYPE                      CDA.ELEMENT_NAME,
    VALUE                           CDA.LONG_ST,
    INTERPETATION_CODE              CDA.CS,
    METHOD_CODE_KEY_ID              CDA.KEY_ID,
    TARGET_SITE_CODE_KEY_ID         CDA.KEY_ID,
    OWNER_INDOC_ID                  CDA.INDOC_ID NOT NULL,
    OWNER_TYPE                      CDA.ELEMENT_NAME,
    OWNER_ASSOCIATION_TYPE          CDA.ELEMENT_NAME,
    TYPE_CODE                       CDA.ST,
    CONTEXT_CONDUCTION_IND          CDA.BL WITH DEFAULT 'TRUE',
    PRIMARY KEY (INDOC_ID, CLINICAL_DOCUMENT_KEY_ID),
    FOREIGN KEY (CLINICAL_DOCUMENT_KEY_ID) REFERENCES
    CDA.CLINICAL_DOCUMENT(KEY_ID) ON DELETE CASCADE ON UPDATE RESTRICT,
    FOREIGN KEY (CODE_KEY_ID) REFERENCES CDA.CODE
    (KEY_ID) ON DELETE SET NULL,
    FOREIGN KEY (UNCERTAINTY_CODE_KEY_ID)
    REFERENCES CDA.MISC_CODE(KEY_ID) ON DELETE SET NULL,
    FOREIGN KEY (LANGUAGE_CODE_KEY_ID) REFERENCES
```

-continued

```
CDA.LANG_CODE(KEY_ID) ON DELETE SET NULL,
    FOREIGN KEY (METHOD_CODE_KEY_ID) REFERENCES
CDA.CODE(KEY_ID) ON DELETE SET NULL,
    FOREIGN KEY (TARGET_SITE_CODE_KEY_ID)
REFERENCES CDA.MISC_CODE(KEY_ID) ON DELETE SET NULL
);
```

Since both component and sourceOf are associations of cardinality 1:n, columns that correspond to their attributes have been added to the class table of the child class, CDA.OBSERVATION in this case. The columns OWNER_IN-DOC_ID, OWNER_TYPE and OWNER_ASSOCIATION-_TYPE have been added to identify, at runtime, the name (XML element) of the actual parent class within cdaEntry.

Returning to the description of FIG. 4, at this stage converter 54 has mapped the associations of the RMIM, as described above. Converter 54 now replaces the distinct types in the relational schema with their corresponding built-in RDB data types, at a type replacement step 80. Although the distinct types are convenient to use in the schema design, they typically degrade the computational efficiency of the RDBMS when querying the RDB at runtime. Therefore, in some embodiments it is preferable to revert to the built-in data types once the relational schema is completed. In other embodiments, type replacement step 80 may be omitted from the method.

In some embodiments, converter 54 produces shredding rules 52 in parallel to the generation of the relational schema in steps 72-80. The generated shredding rules should have a syntax that matches the specific message shredder being used, such as the DB2 XML Extender, cited above. The shredding rules are used at runtime for parsing incoming HL7 messages, extracting data items from these messages and storing the data in RDB 36, as explained in FIG. 1 above.

Having completed the generation of relational schema 46, the method terminates with converter 54 outputting the schema at an output step 82.

Although the embodiments described herein mainly address the conversion of an HL7 CDA RMIM, the principles of the present invention can be used in a similar manner to convert any other HL7 specification to a relational schema. Additionally, the principles of the present invention can be used to convert future versions of the HL7 specifications. These future versions are anticipated to adhere to a similar methodology of deriving specifications from a global RIM and representing messages and documents as XML instances. Similar hierarchically-structured data standards based on general information models can also be converted to relational schemas using the disclosed methods.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for storing communication messages in a relational database, comprising:
   accepting an object model comprising data elements having respective data type definitions and further comprising associations between the data elements, wherein the data elements, the data type definitions and the associations are derived from a hierarchically-structured HL7 specification and comprise at least one data element whose data type definition corresponds to multiple possible data types;
   defining a relational database that represents the object model based on the data elements and the associations;
   receiving a communication message that conforms to the HL7 specification and comprises data items corresponding to one or more of the data elements, including at least one data item having the data type definition that corresponds to the multiple possible data types;
   processing the received communication message so as to identify an actual data type, selected from among the possible data types, to which the at least one data item belongs; and
   storing the data items, including the at least one data item, in the relational database so as to preserve the data type definitions of the data items, including the identified actual data type, and the associations between the data items, as defined in the object model,
   wherein the data elements comprise classes, each having one or more class attributes, wherein defining the relational database comprises creating for each class a respective class table comprising at least one unique identifier in the relational database, and mapping at least one of the class attributes to columns of the class table, and wherein the object model comprises at least one of an association of cardinality 1:n representing a relationship between a parent class and a child class, an association of cardinality n:m representing a relationship between one or more parent classes and one or more child classes, a recursive association representing a relationship between a parent class and a child class wherein the parent class is equal to the child class, and a group association representing a relationship between a group comprising two or more classes and a child class.

2. The method according to claim 1, wherein the hierarchically-structured HL7 specification comprises an HL7 version 3 (HL7 V3) specification, wherein the object model comprises an HL7 Refined Message Information Model (RMIM), and wherein defining the relational database comprises producing a relational schema.

3. The method according to claim 1, wherein defining the relational database comprises producing shredding rules, and wherein storing the data items in the relational database comprises parsing the communication message responsively to the shredding rules so as to extract the data items.

4. The method according to claim 1, wherein accepting the object model comprises accepting information specific to a particular healthcare domain, and wherein defining the relational database comprises applying the domain-specific information so as to represent the data elements and associations.

5. The method according to claim 4, wherein accepting the information comprises at least one of reading the domain-specific information from a configuration file and reading the information embedded in a unified modeling language (UML) profile representing the object model, the profile comprising a UML model augmented with semantic information.

6. The method according to claim 1, wherein the object model comprises a simple data type, and wherein defining the relational database comprises mapping the simple data type to one of a built-in data type and a distinct data type corresponding to the built-in data type in the relational database.

7. The method according to claim 1, wherein the object model comprises a compound data type having two or more attributes, and wherein defining the relational database comprises creating a respective data type table in the relational database, and mapping the attributes to columns of the data type table.

8. The method according to claim 1, wherein the class has an attribute of cardinality n, and wherein mapping the class attributes comprises creating a respective attribute table in the relational database, the respective attribute table comprising a key to the class table, and mapping the attribute of cardinality n to the respective attribute table.

9. The method according to claim 1, wherein the object model comprises the association of cardinality 1:n, wherein the association has one or more 1:n association attributes, and wherein defining the relational database comprises adding columns to the class table corresponding to the child class, the columns comprising a key to the class table corresponding to the parent class and at least one of the one or more 1:n association attributes.

10. The method according to claim 1, wherein the object model comprises the association of cardinality n:m, wherein the association has one or more n:m association attributes, and wherein defining the relational database comprises creating a respective association table in the relational database, the respective association table comprising keys to the class tables corresponding to the parent classes and the child classes and at least one of the one or more n:m association attributes.

11. The method according to claim 1, wherein the object model comprises the recursive association, wherein the association has one or more association attributes, and wherein defining the relational database comprises adding columns to the class table corresponding to the child class, the columns comprising at least one of the one or more association attributes.

12. The method according to claim 1, wherein the object model comprises the group association, wherein the association has one or more group association attributes, and wherein defining the relational database comprises adding columns to the class table corresponding to the child class, the columns comprising an element name of an actual parent class in the group and at least one of the one or more group association attributes.

13. The method according to claim 1, wherein the object model specifies at least one data type defining a data element having an unbounded number of sub-elements, wherein the received communication message comprises at least one data item belonging to the at least one data type having the unbounded number of sub-elements, and wherein storing the data items in the relational database comprises storing the at least one data item belonging to the at least one data type having the unbounded number of sub-elements.

* * * * *